US011603409B2

(12) United States Patent
Youn

(10) Patent No.: US 11,603,409 B2
(45) Date of Patent: Mar. 14, 2023

(54) HUMANIZED DR4 ANTIBODY GENE HAVING APOPTOSIS-INDUCING ACTIVITY AND DUAL-ACTING CHIMERIC ANTIGEN RECEPTOR T CELL OR NATURAL KILLER CELL THERAPEUTIC AGENT USING SAME

(71) Applicant: GENEUIN-TECH CO., LTD., Gimhae-si (KR)

(72) Inventor: Hyun Joo Youn, Gimhae-si (KR)

(73) Assignee: GENEUIN-TECH CO., LTD., Gimhae-si (KR)

( * ) Notice: Subject to any disclaimer, the term of this patent is extended or adjusted under 35 U.S.C. 154(b) by 508 days.

(21) Appl. No.: 16/620,530

(22) PCT Filed: Jun. 5, 2018

(86) PCT No.: PCT/KR2018/006419

§ 371 (c)(1),
(2) Date: Dec. 9, 2019

(87) PCT Pub. No.: WO2018/226020

PCT Pub. Date: Dec. 13, 2018

(65) Prior Publication Data

US 2021/0147563 A1 May 20, 2021

(30) Foreign Application Priority Data

Jun. 9, 2017 (KR) ........................ 10-2017-0072594

(51) Int. Cl.

| | |
|---|---|
| ***C07K 16/28*** | (2006.01) |
| ***A61P 35/00*** | (2006.01) |
| ***A61K 35/17*** | (2015.01) |
| ***A61K 38/17*** | (2006.01) |
| ***A61K 39/395*** | (2006.01) |
| ***C07K 14/725*** | (2006.01) |
| ***C07K 14/705*** | (2006.01) |
| ***A61K 39/00*** | (2006.01) |
| ***A61K 33/243*** | (2019.01) |

(Continued)

(52) U.S. Cl.

CPC ........ *C07K 16/2878* (2013.01); *A61K 31/353* (2013.01); *A61K 31/5377* (2013.01); *A61K 33/243* (2019.01); *A61K 35/17* (2013.01); *A61K 38/177* (2013.01); *A61K 38/1774* (2013.01); *A61K 39/3955* (2013.01); *A61P 35/00* (2018.01); *C07K 14/7051* (2013.01); *C07K 14/70517* (2013.01); *C07K 14/70578* (2013.01); *A61K 2039/572* (2013.01); *C07K 2317/24* (2013.01); *C07K 2317/53* (2013.01); *C07K 2317/622* (2013.01); *C07K 2317/73* (2013.01); *C07K 2317/76* (2013.01); *C07K 2319/02* (2013.01); *C07K 2319/03* (2013.01); *C07K 2319/21* (2013.01); *C07K 2319/30* (2013.01); *C07K 2319/33* (2013.01); *C07K 2319/43* (2013.01)

(58) Field of Classification Search

CPC ............ C07K 16/2878; C07K 14/7051; C07K 14/70517; C07K 14/70578; C07K 2317/24; C07K 2317/53; C07K 2317/622; C07K 2317/73; C07K 2317/76; C07K 2319/02; C07K 2319/03; C07K 2319/21; C07K 2319/30; C07K 2319/33; C07K 2319/43; C07K 2317/75; A61K 35/17; A61K 38/177; A61K 38/1774; A61K 39/3955; A61K 2039/572; A61P 35/00; C12N 5/0638; C12N 5/0646; C12N 2510/00

See application file for complete search history.

(56) References Cited

U.S. PATENT DOCUMENTS

2011/0002933 A1 1/2011 Ashkenazi et al.
2013/0156781 A1 6/2013 Dimitrov et al.

FOREIGN PATENT DOCUMENTS

KR 10-2010-0034353 A 4/2010
KR 10-2011-0041672 A 4/2011

(Continued)

OTHER PUBLICATIONS

Humanization of an agonistic anti-death receptor 4 single chain variable fragment antibody and avidity-mediated enhancement of its cell death-inducing activity.Molecular Immunology 47 (2010) 816-824. (Year: 2010).*

(Continued)

*Primary Examiner* — Amy E Juedes
*Assistant Examiner* — Brian Hartnett
(74) *Attorney, Agent, or Firm* — Revolution IP, PLLC

(57) ABSTRACT

The present invention relates to a humanized DR4 antibody gene having apoptosis-inducing activity, and a dual-acting chimeric antigen receptor T cell or natural killer cell therapeutic agent, a secretory DR4 scFv antibody recombinant protein synthesized by using a humanized DR4 scFv antibody gene (humanized anti-DR4 scFv) may be used as an anticancer drug specifically targeting DR4 by binding to DR4 expressed on surface of the cancer cells to induce apoptosis of the cancer cells. In addition, the chimeric antigen receptor (CAR) using the humanized DR4 scFv antibody gene is predicted to have a strong anticancer immune effect as a dual-acting cell therapeutic agent, which is capable of simultaneously inducing apoptosis in cancer cells by DR4 and exhibiting a cytotoxic effect for cytotoxic T lymphocytes or natural killer cells by binding to DR4 expressed on the surface of cancer cells, as a DR4-specific CAR-T cell or CAR-NK cell therapeutic agent.

10 Claims, 10 Drawing Sheets

Specification includes a Sequence Listing.

(51) Int. Cl.
*A61K 31/353* (2006.01)
*A61K 31/5377* (2006.01)

(56) References Cited

FOREIGN PATENT DOCUMENTS

| | | | |
|---|---|---|---|
| KR | 10-1077608 | B1 | 10/2011 |
| WO | 2016/201300 | A1 | 12/2016 |

OTHER PUBLICATIONS

Kobayashi et al.A chimeric antigen receptor for TRAIL-receptor 1 induces apoptosis in various types of tumor cellsBiochemical and Biophysical Research Communications 453 (2014) 798-803 (Year: 2014).*
Lee et al.Humanization of an agonistic anti-death receptor 4 single chain variablefragment antibody and avidity-mediated enhancement of its cell death-inducing activity.Molecular Immunology 47 (2010) 816-824 (Year: 2010).*
Eiji Kobayahshi et al, “A chimeric antigen receptor for TRAIL-receptor 1 induces apoptosis in various types of tumor cells”, Biochem Biophys Res Commun. Oct. 31, 2014; 453(4):798-803. doi: 10.1016/j.bbrc.2014.10.024. Epub Oct. 14, 2014.
International Search Report for PCT/KR2018/006419 dated Nov. 13, 2018 from Korean Intellectual Property Office.
Lee, Seung-Hyun et al, “Humanization of an agonistic anti-death receptor 4 single chain variable fragment antibody and avidity-mediated enhancement of its cell death-inducing activity”, Molecular Immunology, 2010, vol. 47, No. 4, pp. 816-824.

* cited by examiner

[FIG. 1]

(A) SEQ ID NO: 1

EVQLVESGGGLVQPGGSLRLSCSASGFTFSSYSMQWVRQAPGKGLEYVAGIRSDGRYTNYGAAVKGRATI
SRDNSKNTVYLQMNSLRAEDTAVYYCAKGAYGYCGSTCAPYLGQIDAWGQGTLVTVSSGSTSGSGKPGS
GEGSTKGSYELTQPPSVSVSPGQTVRITCSGGRYTYGWFQQKPGQAPVTVIYGNDKRPSNIPSRFSGSTSG
STVTLTISGVQAEDEADYYCGGADFSAGLFGGGTKLTVL (B) SEQ ID NO: 2 gaagtccaacttgtagaatcaggcggcgggctcgtacagcccggtggaagccttagactttcttgttcagcctcagggtttacattctccag
ttactccatgcaatgggtgcggcaagcgcccggaaaagggcttgaatacgtggcgggtatcagaagcgacggtcgatatacaaactacg
gcgctgcggtaaaaggccgcgctaccatatctcgcgataactcaaagaataccgtctatctccagatgaacagccttagagcggaagat
accgcagtgtattattgtgctaagggtgcatacggttactgtggatctacctgtgcaccgtacctcggccagatagatgcatgggggcaag
gcacgttggtcactgtatcaagtgggagcacttctggaagtgggaagcctggggagcggggggaaggcagcaccaaaggttcatatgagctt
acccaacctccgtccgtctccgttagcccaggtcagacagttagaataacctgcagtggaggacgatacacgtacggctggtttcaaca
aaagccgggggcaagcgccggtgacagttatctatgggaatgataaaaggccatctaatataccgtctcgattttcaggctctacttctggc
agtactgtaacactcacgattagtggggtccaagcagaagatgaggcagactattactgcgggggcgcagatttctcagcgggcctttttg
gaggggggtacaaagctcacggtgctg

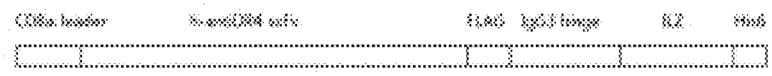

(B) Complete sequence (SEQ ID NO: 3)

atggccttgcctgttactgcgttgctgctgccccttgcactgttgctccacgcggccagaccagaagtccaacttgt
agaatcaggcggcgggctcgtacagcccggtggaagccttagactttcttgttcagcctcagggtttacattctcc
agttactccatgcaatgggtgcggcaagcgcccggaaaagggcttgaatacgtggcgggtatcagaagcgacg
gtcgatatacaaactacggcgctgcggtaaaaggccgcgctaccatatctcgcgataactcaaagaataccgtc
tatctccagatgaacagccttagagcggaagataccgcagtgtattattgtgctaagggtgcatacggttactgtg
gatctacctgtgcaccgtacctcggccagatagatgcatgggggcaaggcacgttggtcactgtatcaagtggga
gcacttctggaagtgggaagcctgggagcggggaaggcagcaccaaaggttcatatgagcttacccaacctcc
gtccgtctccgttagcccaggtcagacagttagaataacctgcagtggaggacgatacacgtacggctggtttca
acaaaagccggggcaagcgccggtgacagttatctatgggaatgataaaaggccatctaatataccgtctcgatt
ttcaggctctacttctggcagtactgtaacactcacgattagtggggtccaagcagaagatgaggcagactattac
tgcgggggcgcagatttctcagcgggcctttttggagggggtacaaagctcacggtgctggccgcagccgacta
caaggatgacgatgataaggggggcggcaccgaaacccatccacaccgccccggcagctcacggatgaagcaaa
ttgaagacaagattgaagaaatacttagtaagatttaccatatcgaaaacaaaatcgctcgcattaagaaacttat
aggtgaacgccatcaccaccaccaccac sequence separation CD8α leader sequence (SEQ ID NO: 4)

atggccttgcctgttactgcgttgctgctgccccttgcactgttgctccacgcggccagacca h-antiDR4 scFv sequence (SEQ ID NO: 2)

gaagtccaacttgtagaatcaggcggcgggctcgtacagcccggtggaagccttagactttcttgttcagcctca
gggtttacattctccagttactccatgcaatgggtgcggcaagcgcccggaaaagggcttgaatacgtggcgggt
atcagaagcgacggtcgatatacaaactacggcgctgcggtaaaaggccgcgctaccatatctcgcgataactc
aaagaataccgtctatctccagatgaacagccttagagcggaagataccgcagtgtattattgtgctaagggtgc
atacggttactgtggatctacctgtgcaccgtacctcggccagatagatgcatgggggcaaggcacgttggtcac
tgtatcaagtgggagcacttctggaagtgggaagcctgggagcggggaaggcagcaccaaaggttcatatgag
cttacccaacctccgtccgtctccgttagcccaggtcagacagttagaataacctgcagtggaggacgatacac
gtacggctggtttcaacaaaagccggggcaagcgccggtgacagttatctatgggaatgataaaaggccatcta
atataccgtctcgatttcaggctctacttctggcagtactgtaacactcacgattagtggggtccaagcagaagat
gaggcagactattactgcgggggcgcagatttctcagcgggcctttttggagggggtacaaagctcacggtgctg FLAG sequence (SEQ ID NO: 5)

gccgcagccgactacaaggatgacgatgataagggg

IgG3 hinge sequence (SEQ ID NO: 6)

gcggcaccgaaacccatccacaccgccccggcagctcacgg

ILZ sequence (SEQ ID NO: 7)

atgaagcaaattgaagacaagattgaagaaatacttagtaagatttaccatatcgaaaacaaaatcgctcgcatt
aagaaacttataggtgaacgc His6 sequence (SEQ ID NO: 8)

catcaccaccaccaccac

[FIG. 3]
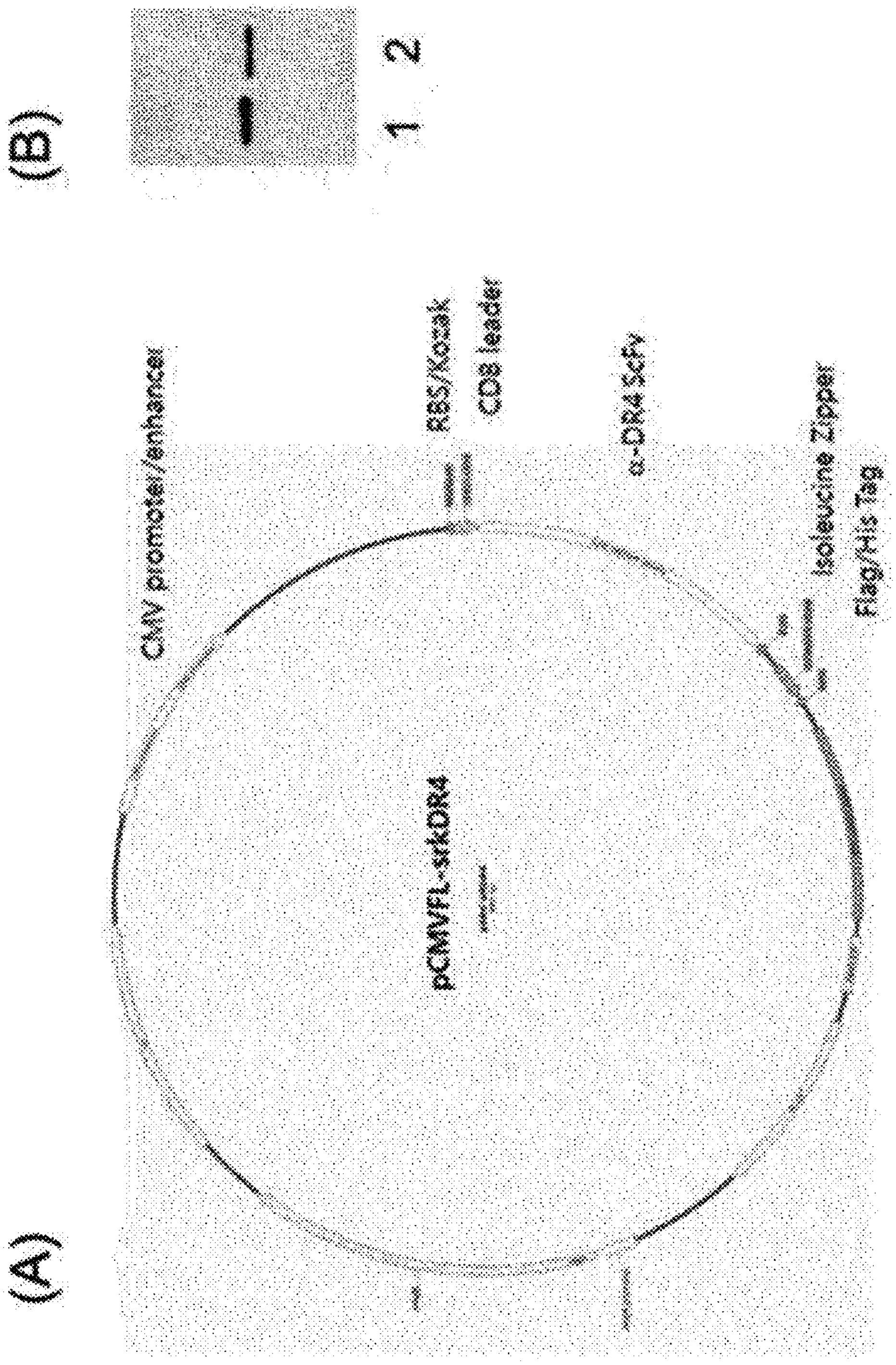

[FIG. 4]
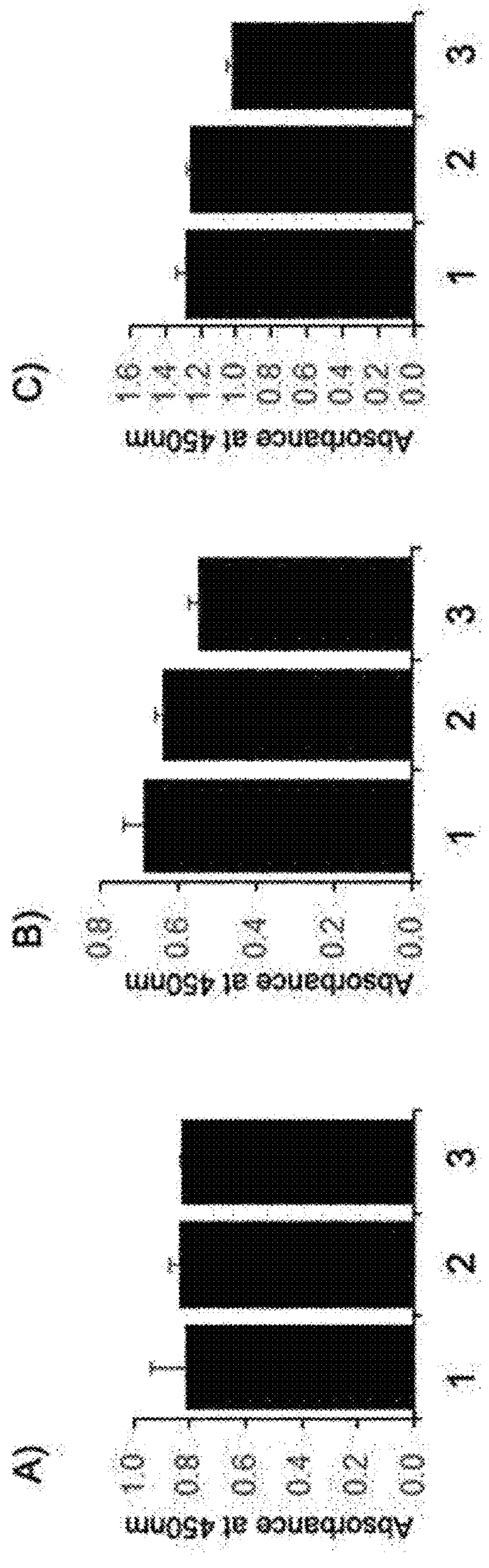

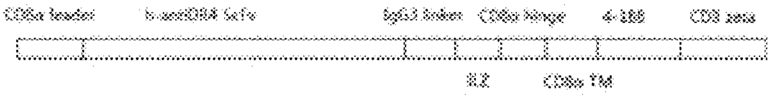

(B) Complete sequence (SEQ ID NO: 9)

atggccttgcctgttactgcgttgctgctgccccttgcactgttgctccacgcggccagaccagaagtccaacttgt
agaatcaggcggcgggctcgtacagcccggtggaagccttagactttcttgttcagcctcagggtttacattctcc
agttactccatgcaatgggtgcggcaagcgcccggaaaagggcttgaatacgtggcgggtatcagaagcgacg
gtcgatatacaaactacggcgctgcggtaaaaggccgcgctaccatatctcgcgataactcaaagaataccgtc
tatctccagatgaacagccttagagcggaagataccgcagtgtattattgtgctaagggtgcatacggttactgtg
gatctacctgtgcaccgtacctcggccagatagatgcatggggggcaaggcacgttggtcactgtatcaagtggga
gcacttctggaagtgggaagcctgggagcggggaaggcagcaccaaaggttcatatgagcttacccaacctcc
gtccgtctccgttagcccaggtcagacagttagaataacctgcagtggaggacgatacacgtacggctggtttca
acaaaagccggggcaagcgccggtgacagttatctatgggaatgataaaaggccatctaatataccgtctcgatt
ttcaggctctacttctggcagtactgtaacactcacgattagtggggtccaagcagaagatgaggcagactattac
tgcgggggcgcagatttctcagcgggcctttttggagggggtacaaagctcacggtgctggcggcaccgaaacc
atccacaccgcccggcagctcacggatgaagcaaattgaagacaagattgaagaaatacttagtaagatttacc
atatcgaaaacaaaatcgctcgcattaagaaacttataggtgaacgcaccacgaccccagcaccacggccgc
cgactccggccccgacgatagcctcacaacctctgtctttgcgccctgaagcgtgccgacctgcagcaggcggt
gccgtacatacgagagggctggatttgcttgcgacatttatatttgggctcccctcgcagggacatgtggcgtatt
gcttctctctctcgtgatcacgctctattgcaaaaggggggcgaaagaagttgctgtatatctttaaacaaccatttat
gagaccagtgcaaacaacgcaggaggaagatggctgtagctgtaggttccccgaagaggaggaaggaggctg
cgaactcagggttaagttcagtagatctgcggatgctcccgcgtatcagcagggccagaatcagctttacaatga
actcaatcttggccgccgagaagagtatgatgtgctcgacaagcgccgcggcagagaccccgaaatgggaggt
aagcccaggagaaaaaatccgcaggaaggtctttacaacgaattgcaaaaggacaagatggcagaagcatac
tcagagattggtatgaaaggtgaacggcgacgcgggaaaggacatgacggcctttatcaaggactctcaaccg
ctactaaagatacttacgacgcgctccacatgcaggctctgccaccgcgc

[FIG. 6]

sequence separation

CD8α leader sequence (SEQ ID NO: 4)
atggccttgcctgttactgcgttgctgctgccccttgcactgttgctccacgcggccagacca h-antiDR4 scFv sequence (SEQ ID NO: 2)
gaagtccaacttgtagaatcaggcggcgggctcgtacagcccggtggaagccttagactttcttgttcagcctca
gggtttacattctccagttactccatgcaatgggtgcggcaagcgcccggaaaagggcttgaatacgtggcgggt
atcagaagcgacggtcgatatacaaactacggcgctgcggtaaaaggccgcgctaccatatctcgcgataactc
aaagaataccgtctatctccagatgaacagccttagagcggaagataccgcagtgtattattgtgctaagggtgc
atacggttactgtggatctacctgtgcaccgtacctcggccagatagatgcatggggcaaggcacgttggtcac
tgtatcaagtgggagcacttctggaagtgggaagcctgggagcggggaaggcagcaccaaaggttcatatgag
cttacccaacctccgtccgtctccgttagcccaggtcagacagttagaataacctgcagtggaggacgatacac
gtacggctggtttcaacaaaagccggggcaagcgccggtgacagttatctatgggaatgataaaaggccatcta
atataccgtctcgattttcaggctctacttctggcagtactgtaacactcacgattagtggggtccaagcagaagat
gaggcagactattactgcgggggcgcagatttctcagcgggccttttggaggggggtacaaagctcacggtgctg IgG3 hinge sequence (SEQ ID NO: 6)
gcggcaccgaaaccatccacaccgcccggcagctcacgg ILZ sequence (SEQ ID NO: 7)
atgaagcaaattgaagacaagattgaagaaatacttagtaagatttaccatatcgaaaacaaaatcgctcgcatt
aagaaacttataggtgaacgc CD8a hinge sequence (SEQ ID NO: 10)
accacgacccccagcaccacggccgccgactccggccccgacgatagcctcacaacctctgtctttgcgccctg
aagcgtgccgacctgcagcaggcggtgccgtacatacgagagggctggattttgcttgcgac CD8a TM sequence (SEQ ID NO: 11)
atttatatttgggctcccctcgcagggacatgtggcgtattgcttctctctctcgtgatcacgctctattgc 4-1BB signal sequence (SEQ ID NO: 12)
aaaagggggcgaaagaagttgctgtatatctttaaacaaccatttatgagaccagtgcaaacaacgcaggagga
agatggctgtagctgtaggttccccgaagaggaggaaggaggctgcgaactc CD3 zeta Signal sequence (SEQ ID NO: 13)
agggttaagttcagtagatctgcggatgctcccgcgtatcagcagggccagaatcagctttacaatgaactcaat
cttggccgccgagaagagtatgatgtgctcgacaagcgccgcggcagagaccccgaaatgggaggtaagccc
aggagaaaaaatccgcaggaaggtctttacaacgaattgcaaaaggacaagatggcagaagcatactcagag
attggtatgaaaggtgaacggcgacgcgggaaaggacatgacggcctttatcaaggactctcaaccgctactaa
agatacttacgacgcgctccacatgcaggctctgccaccgcgc

[FIG. 7]
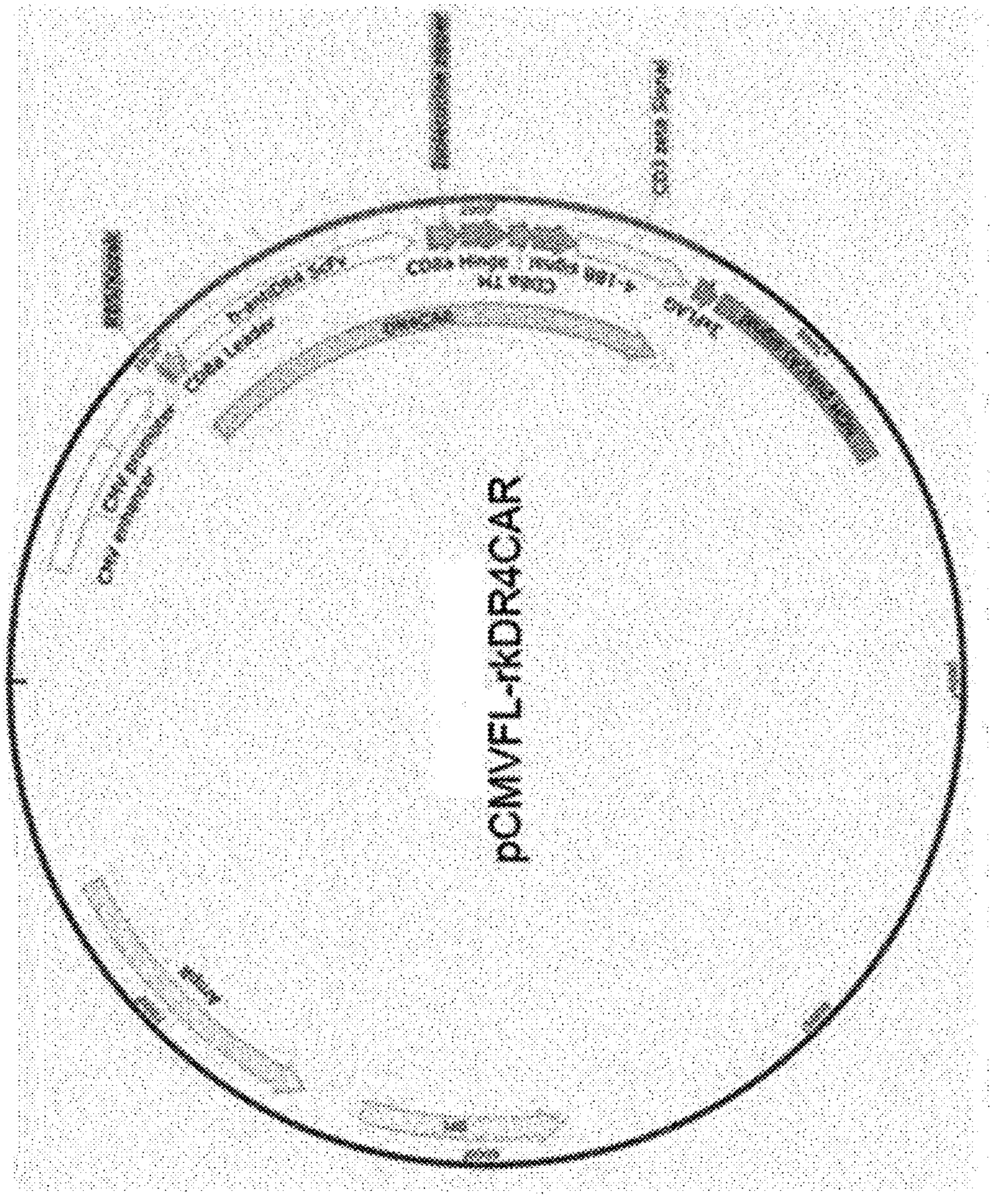

[FIG. 8]
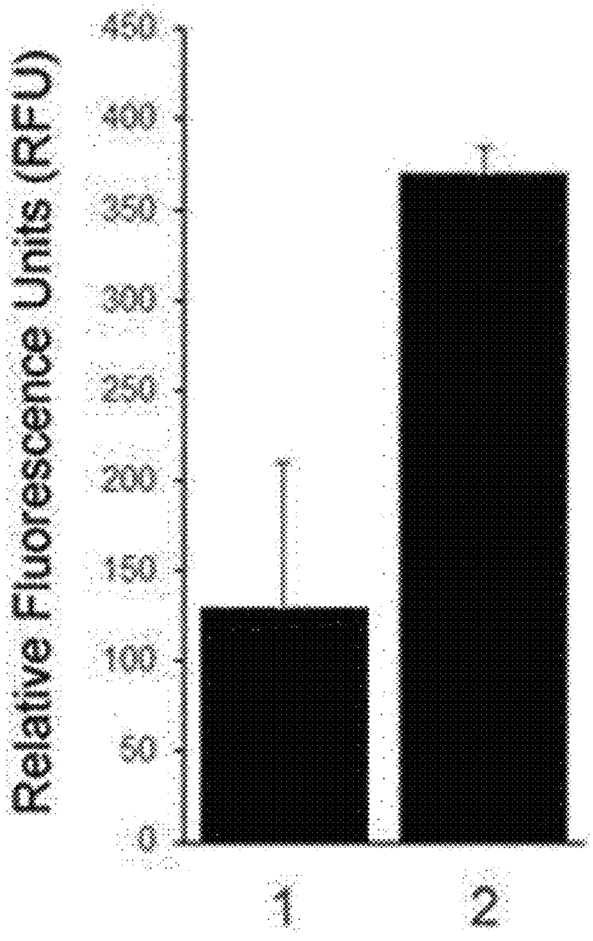

[FIG. 9]
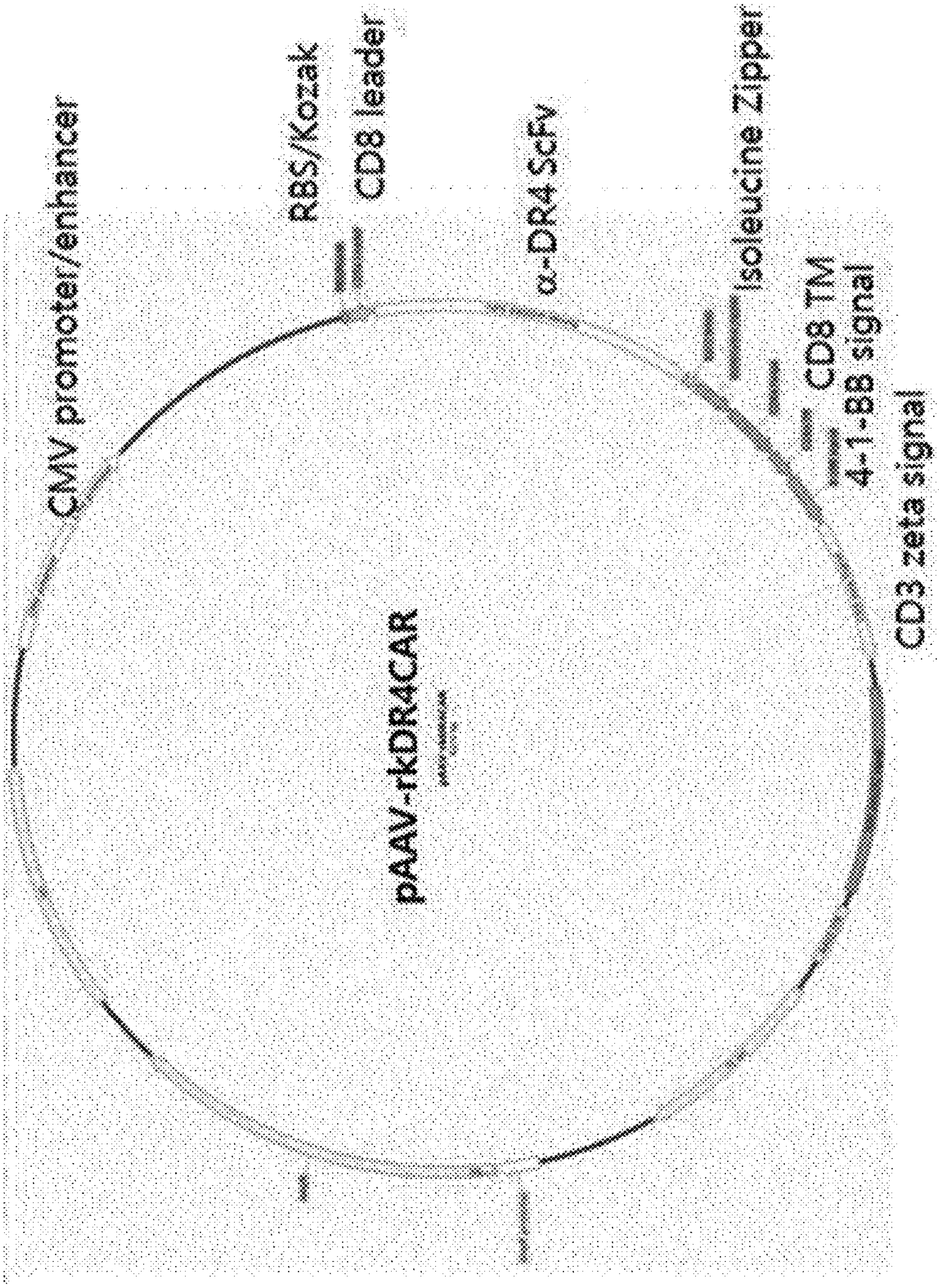

[FIG. 10]
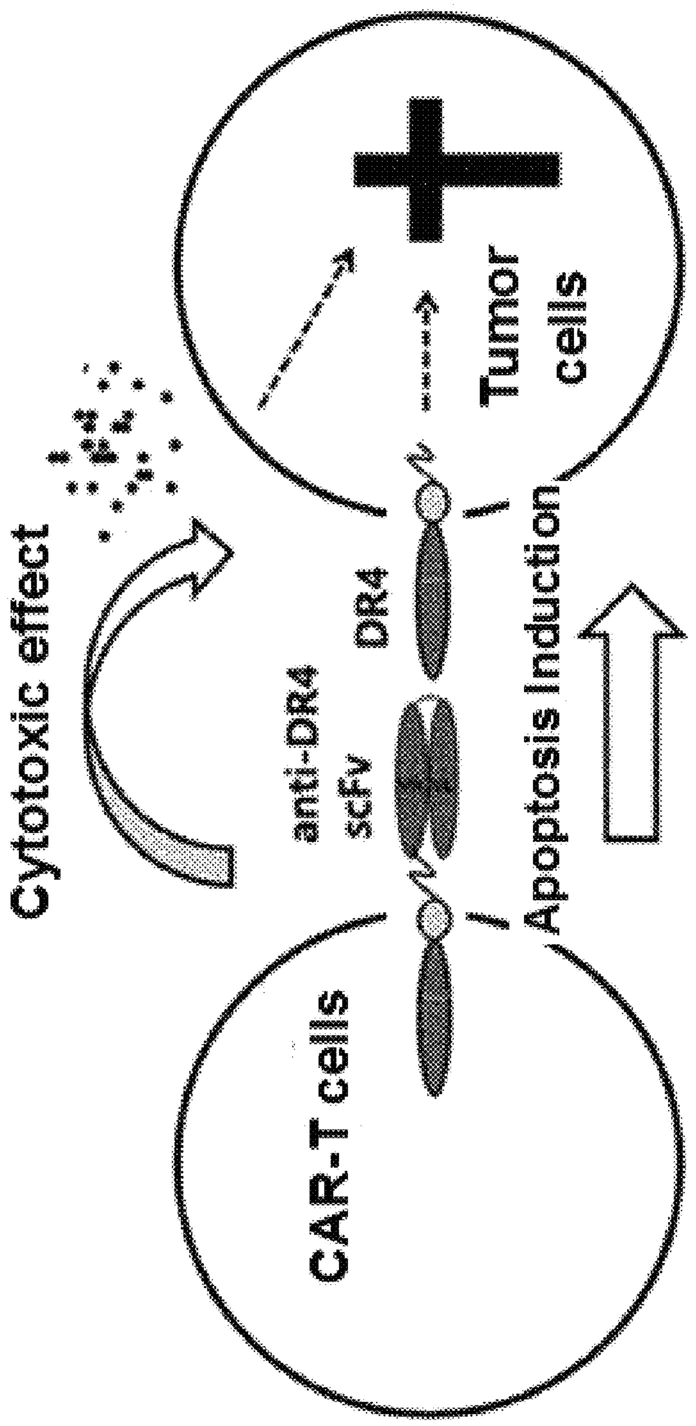

HUMANIZED DR4 ANTIBODY GENE HAVING APOPTOSIS-INDUCING ACTIVITY AND DUAL-ACTING CHIMERIC ANTIGEN RECEPTOR T CELL OR NATURAL KILLER CELL THERAPEUTIC AGENT USING SAME

CROSS REFERENCE TO PRIOR APPLICATIONS

This application is a National Stage Application of PCT International Patent Application No. PCT/KR2018/006419 filed on Jun. 5, 2018, under 35 U.S.C. § 371, which claims priority to Korean Patent Application No. 10-2017-0072594 filed on Jun. 9, 2017, which are all hereby incorporated by reference in their entirety.

TECHNICAL FIELD

The present invention relates to a humanized DR4 antibody gene having apoptosis inducing activity, and a dual-acting chimeric antigen receptor T cell or natural killer cell therapeutic agent using the same.

BACKGROUND ART

A cell therapeutic agent using chimeric antigen receptor T cells (CAR-T) among anticancer cell therapeutic agents is an anticancer immune cell therapy using T cells that kill cancer cells and is a new chemotherapy that can give hope for the treatment of terminal cancer. CAR-T anti-cancer immune cell therapeutic agent is a new concept of cancer therapy that introduces chimeric antigen receptors (CARs) that bind to cancer-specific antigens contained in cancer cells into T cells so that T cells can effectively recognize and kill cancer cells. It is a next-generation cancer therapeutic agent that maximizes cancer cell killing ability by giving a new ability recognizing cancer cell to cytotoxic T lymphocyte (CTL).

CTL is a cell that collects in cancer tissues and specifically recognizes and kills only cancer cells, and is very important for tumor immunity. CTL has a T cell receptor (TCR) that recognizes cancer cells on the surface of the cell, and kills the cancer cells in response to cancer antigens caused by the cancer cells. However, as cancer cells become more and more malignant, the cancer cells have the ability to conceal antigens so that cancer cells prevent TCR from reacting with cancer antigens, thereby occasionally avoiding the killing action by CTL.

To overcome this problem, a technique has been developed in which an antibody gene capable of binding directly and strongly to cancer cells is inserted into a CTL, and the CTL reacts with cancer cells antigen through this antibody to kill the cancer cells. Antibodies against cancer antigens introduced into CTL for this purpose are called chimeric antigen receptors (CAR), and CTL that are engineered to kill cancer cells by expressing the antibody protein on the cell surface are called CAR-T cells. In addition, cells which are engineered to kill cancer cells by expressing chimeric antigen receptors on the surface of natural killer cells (NK cells) are called CAR-NK.

In order to induce cancer cell killing after CAR-T cells react with cancer cells, the intracellular region of the CAR cancer antigen receptor molecule must have a protein region must have a protein region activating the ability killing CTL, i.e. a signal domain. For this purpose, a method of incorporating a gene into T cells by binding signal domain capable of inducing cell activity in T cells to a CAR gene. Because CAR-T cells prepared by the above method have T cell signal domain for new cancer antigen receptors and antibodies, if the antibody recognizes cancer cells, T cell activation proceeds to kill cancer cells. Currently, the CAR-T therapeutic agents are mainly aimed at improving these signal domains. Early developed first generation CAR-T cells had one signal domain in the CAR structure, but studies are underway to increase the killing capacity of CAR-T cells by attaching more signal domains.

To produce CAR-T cells that target cancer cells, a monoclonal antibody specific for the cancer antigen is required, and only the antigen-binding site of the antibody must be manipulated into a single chain variable fragment (scFv) and this scFv antibody fragments should be manipulated similarly to human antibody fragments. A novel antigen receptor in which the signaling domain of the T cell initiating the killing signaling process in CTL is coupled to this engineered scFv must be developed.

To date, CAR-T cells with fragments of scFv antibodies against CD19 have been developed, and clinical trials for the treatment of drug-resistant acute lymphocytic leukemia have been successfully conducted and CAR-T cells for other antigens are also being developed. Up to now, CAR-T cell therapies that recognize cancer cell antigens, such as CD20, CD22, CD30, ROR1, K light chain, CD123, CD33, CD133, CD138, B cell mutant antigens and the like, have been studied, however there are no studies on CAR-T cell therapies targeting death receptor 4 (DR4). In addition, a CAR-T cell therapeutic agent can be utilized as a CAR-NK cell therapeutic agent by applying the concept thereof to natural killer cells and introducing CAR into natural killer cells.

DISCLOSURE

Technical Problem

An object of the present invention is to provide a DR4 specific target anticancer agent using a humanized DR4 scFv antibody gene and a chimeric antigen receptor expressing T cell or natural killer cell immune anticancer agent using the humanized DR4 scFv antibody gene.

Technical Solution

In order to achieve the above object, the present invention provides a humanized anti-DR4 antibody fragment, a recombinant protein using the same, and a pharmaceutical composition for treating cancer comprising the recombinant protein as an active ingredient.

The present invention also provides a humanized anti-DR4 antibody fragment, chimeric antigen receptor expressing T cells or natural killer cells using the same, and a pharmaceutical composition for treating cancer comprising the cells as an active ingredient.

Advantageous Effects

According to the present invention, the secretory DR4 scFv antibody recombinant protein synthesized using a humanized anti-DR4 scFv antibody gene can be utilized as a DR4-specific target anticancer agent by binding to DR4 expressed on the surface of cancer cells and inducing death of cancer cells.

In addition, the chimeric antigen receptor (CAR) using the humanized DR4 scFv antibody gene is utilized as a DR4-specific CAR-T cell or CAR-NK cell therapeutic agents, and can be expected to have a potent immuno-cancer effect as a dual-acting cell therapeutic agent having for a strong immune anticancer effect since it exhibits the induction of apoptosis of cancer cells and the cytotoxicity of cytotoxic T lymphocytes or natural killer cells by DR4 by binding to DR4 expressed on the surface of cancer cells simultaneously. In addition, chemotherapy, radiation therapy and the like used in cancer treatment often increase the expression of DR4 in cancer cells, thus the DR4 specific CAR-T cells or CAR-NK cells can be utilized as a new method for treating refractory cancer in combination with conventional anticancer agents or radiation therapy.

DESCRIPTION OF DRAWINGS

FIG. 1 shows the amino acid sequence (A) and the nucleotide sequence of the humanized DR4 scFv antibody protein.

FIG. 2 shows the antibody gene structure for the formation of trimolecular complexes of secretory humanized DR4 scFv antibody recombinant protein (A) and its complete nucleotide sequence and the nucleotide sequence of each domain (B).

FIG. 3 illustrates (A) which shows the structure of the secretory humanized DR4 scFv antibody recombinant protein expression vector and (B) which shows the results confirming the presence of the DR4 scFv antibody recombinant protein secreted in the culture medium by the Western blotting (1: DR4 scFv antibody recombinant protein purified by using His tag, 2: DR4 scFv antibody recombinant protein secreted in the culture medium of the transformed cell).

FIG. 4 shows the effect of inducing apoptosis of noncancer cells or DR4 expression cancer cells by secretory humanized DR4 scFv antibody recombinant protein, (A) is the effect on HEK293 cells, embryonic-derived cell line that does not express DR4 as a control, (B) and (C) show the effect of inducing apoptosis on HeLa cells and HCT-116 cells, which are cancer cell lines expressing DR4 (1: control, 2 and 3: secretory humanized DR4 scFv antibody recombinant protein purified by using His tag at low and high concentrations).

FIG. 5 shows the humanized DR4 scFv chimeric antigen receptor (CAR) expression gene structure (A) and its complete nucleotide sequence (B).

FIG. 6 shows the complete nucleotide sequence of FIG. 5(B) for each domain.

FIG. 7 shows the structure of the CAR expression plasmid vector using FIG. 5(A).

FIG. 8 shows induction effect of apoptosis of HeLa cells, DR4 expression cancer cell lines, or HEK293 Cells, an embryonic-derived cell line which does not express DR4, by lymphocytes, after injecting the CAR expression plasmid vector of FIG. 7 into splenocytes of the mouse to prepare DR4 specific chimeric antigen receptor expression lymphocytes (1: HEK293 cells (control) not expressing DR4, 2: HeLa cells expressing DR4 (experimental group)).

FIG. 9 shows the structure of the recombinant viral vector using FIG. 5(A).

FIG. 10 shows conceptual diagram for killing the cancer cell of the dual acting chimeric antigen receptor T cell therapeutic agent.

BEST MODE

The inventors of the present invention confirmed the cancer cell death effect of the secretory DR4 scFv antibody fragment recombinant protein using the humanized DR4 scFv antibody gene, and the dual-acting immune anticancer effect of cancer cell death and cytotoxicity of chimeric antigen receptor expression T cells using humanized DR4 scFv antibody gene, and completed the present invention.

As used herein, the term "antibody" refers to an immunoglobulin molecule that specifically binds to an antigen. The antibody may be a complete immunoglobulin derived from a natural or recombinant source and may be an immunoreactive portion of the complete immunoglobulin. Antibodies are often of immunoglobulin molecules. Antibodies of the present invention may exist in various forms, including, for example, polyclonal antibodies, monoclonal antibodies, Fv, Fab and F(ab)2, as well as single chain antibodies and humanized antibodies.

As used herein, the term "antibody fragment" refers to a portion of a complete antibody and refers to an antigenic determining variable region of the complete antibody. Examples of antibody fragments include, but are not limited to, Fab, Fab', F(ab')2 and Fv fragments, linear antibodies, scFv antibodies, and multispecific antibodies formed from antibody fragments.

As used herein, the term "scFv (single-chain Fv, single chain fragment antibody or antibody fragment)" refers to an antibody connecting variable regions of light and heavy chains. In some cases, it may include a linker (linking region) consisting of a peptide chain in which about 15 amino acids are linked, wherein the scFv may have the structure of a light chain variable region-linking region-heavy chain variable region, or heavy chain variable region-linking region-light chain variable region and has the same or similar antigenic specificity as the original antibody.

As used herein, the term "variable region" refers to a site that exhibits many variations in the sequence while performing a function of specifically binding to an antigen, and generally includes complementarity determining regions (CDR) and a framework region (FR).

As used herein, the term "antibody heavy chain" refers to two larger polypeptide chains present in all antibody molecules in their naturally occurring form.

As used herein, the term "antibody light chain" refers to two smaller polypeptide chains present in all antibody molecules in their naturally occurring form. κ and λ light chains refer to two major antibody light chain isotypes.

As used herein, the term "antibody (or scFv) library" is a collection of various antibody genes having different sequences. Very high diversity is required to isolate antibodies specific for any antigen from an antibody library, and libraries consisting of different antibody clones are constructed and used. The antibody gene constituting such an antibody library, for example can be cloned into a phagemid vector and transfected into a transformant (*E. coli*).

As used herein, the term "vector" is a composition of materials that include an isolated nucleic acid and can be used to deliver the isolated nucleic acid into the interior of a cell. Many vectors are known in the art, including but not limited to, polynucleotides, plasmids, and viruses associated with linear polynucleotides, ionic or amphiphilic compounds. Thus, the term "vector" includes autonomously replicating plasmids or viruses. The term should also be understood to include non-plasmid and non-viral compounds that facilitate the delivery of nucleic acids into cells, such as polylysine compounds, liposomes and the like. Examples of viral vectors include, but are not limited to, adenovirus vectors, adeno-associated virus vectors, retroviral vectors, and the like.

As used herein, the term "CAR-T cell" is a new concept of cancer therapy that inserts a chimeric antigen receptor (CAR) that binds to a cancer-specific antigen of cancer cells into T cells, thereby allowing T cells to effectively recognize and kill cancer cells, and it is an anticancer immunity cell therapeutic agent which maximizes cancer cell killing ability by giving new cancer cell recognizing ability to cytotoxic T lymphocyte (CTL).

The present invention provides an anti-DR4 antibody fragment recombinant protein expression cassette comprising an anti-DR4 antibody fragment domain specifically binds to a death receptor (DR4), a trimolecular complex forming domain and a secretory inducing domain.

Preferably, the trimolecular complex forming domain may be an isoleucine zipper domain, but it is not limited thereto.

Preferably, the secretory inducing domain is for secreting the protein out of the cell, and may be a CD8α chain leader sequence domain, but it is not limited thereto.

Preferably, the anti-DR4 antibody fragment may have a nucleotide sequence of SEQ ID NO: 2.

Preferably, the anti-DR4 antibody fragment may be selected from the group consisting of scFv, (scFv)2, Fab, Fab' and F(ab')2, but it is not limited thereto.

Preferably, the anti-DR4 antibody fragment recombinant protein expression cassette may have a nucleotide sequence of SEQ ID NO: 3.

The present invention also provides a recombinant viral vector comprising the anti-DR4 antibody fragment recombinant protein expression cassette.

The present invention also provides a cell transformed with the recombinant viral vector.

The present invention also provides an anti-DR4 antibody fragment recombinant protein secreted from the transformed cells.

Preferably, the anti-DR4 antibody fragment recombinant protein may be a trimolecular complex.

Preferably, the anti-DR4 antibody fragment recombinant protein may specifically bind to DR4 expressed on the surface of cancer cells to induce the apoptosis of cancer cells.

Also, the present invention provides a pharmaceutical composition for treating cancer comprising the transformed cell or the anti-DR4 antibody fragment recombinant protein secreted from the transformed cell, as an active ingredient.

In addition, the present invention provides an anti-DR4 antibody fragment recombinant protein expression cassette comprising an anti-DR4 antibody fragment domain specifically binds to a death receptor (DR4), a trimolecular complex forming domain, a secretory inducing domain, a transmembrane domain and a signaling domain.

Preferably, the trimolecular complex forming domain may be an isoleucine zipper domain, but it is not limited thereto.

Preferably, the secretory inducing domain is for secreting the protein out of the cell, and may be a CD8α chain leader sequence domain, but it is not limited thereto.

Preferably, the transmembrane domain is for binding the protein to the cell membrane, and may be 8α TM transmembrane domain, but it is not limited thereto.

Preferably, the signaling domain is for cytotoxic activation signaling, and may be the 4-1BB/CD3 zeta signaling domain, but it is not limited thereto.

Preferably, the anti-DR4 antibody fragment recombinant protein may be a chimeric antigen receptor (CAR).

Preferably, the anti-DR4 antibody fragment may have a nucleotide sequence of SEQ ID NO: 2.

Preferably, the anti-DR4 antibody fragment may be selected from the group consisting of scFv, (scFv)2, Fab, Fab' and F(ab')2, but it is not limited thereto.

Preferably, the anti-DR4 antibody fragment recombinant protein expression cassette may have a nucleotide sequence of SEQ ID NO: 9.

Furthermore, the present invention provides a vector comprising the anti-DR4 antibody fragment recombinant protein expression cassette.

Preferably, the vector may be a recombinant plasmid vector or a recombinant viral vector.

Preferably, the recombinant viral vector may be selected from the group consisting of adenovirus vectors, adeno-associated viral vectors, lentiviral vectors and retroviral vectors, but it is not limited thereto.

The present invention also provides chimeric antigen receptor expressing cell transformed with the vector.

Preferably, the chimeric antigen receptor expressing cell may be chimeric antigen receptor expressing T (CAR-T) cell or natural killer (CAR-NK) cell.

In addition, the present invention provides a pharmaceutical composition for treating cancer comprising the chimeric antigen receptor expressing cell as an active ingredient.

Preferably, the chimeric antigen receptor expressing cell expresses a CAR on the surface of cell, and the CAR specifically binds to DR4 expressed on the surface of cancer cell to induce apoptosis of the cancer cell.

Preferably, the chimeric antigen receptor expressing cell may enhance cancer cell killing ability by activating cytotoxicity.

The present invention also provides a pharmaceutical composition for treating cancer using the chimeric antigen receptor expressing cell in combination with an anticancer agent or radiation therapy.

Preferably, the chimeric antigen receptor expressing cell may be chimeric antigen receptor expressing T (CAR-T) cell or natural killer (CAR-NK) cell.

Preferably, the anticancer agent or radiation therapy may increase DR4 expression on the surface of cancer cells.

Preferably, the anticancer agent may be selected from the group consisting of cisplatin, apigenin, and gefitinib, but it is not limited thereto.

When the composition of the present invention is a pharmaceutical composition, it may further comprise a suitable carrier, excipient or diluent commonly used in the manufacture of the pharmaceutical composition.

Examples of the carrier, excipient and diluent which can be used in the present invention, include lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate or mineral oil and the like.

The compositions can be used by formulating in the form of oral formulations such as powders, granules, tablets, capsules, suspensions, emulsions, syrups, aerosols and the like, external preparation, suppositories, and sterile injectable solutions, respectively, according to conventional methods.

When formulated, fillers, extenders, binders, wetting agents, disintegrating agents and diluents such as surfactants or excipients are usually used and formulated. Solid formulations for oral administration include tablets, pills, powders, granules, capsules, etc., and such solid formulations may contain at least one excipient such as starch, calcium carbonate, sucrose or lactose, gelatin and the like.

In addition to simple excipients, lubricants such as magnesium stearate and talc are also used. Examples of the liquid formulations for oral administration include suspensions, solutions, emulsions, syrups and the like, and various excipients such as wetting agents, sweeteners, fragrances, preservatives and the like may be included in addition to water and liquid paraffin which are commonly used as simple diluents.

Formulations for parenteral administration include sterile aqueous solutions, non-aqueous solutions, suspensions, emulsions, freeze-dried preparations, and suppositories. Examples of the non-aqueous solution and the suspension include propylene glycol, polyethylene glycol, vegetable oil such as olive oil, injectable ester such as ethyl oleate, and the like. As the base of the suppository, witepsol, macrogol, tween 61, cacao butter, laurinum, glycerogelatin and the like can be used.

The amount of the composition may vary depending on the age, sex, and weight of the patient, but the amount of 0.1 to 2.0 mg/kg may be administered once to several times daily.

In addition, the dosage of such a composition can be increased or decreased depending on the route of administration, the severity of the disease, sex, weight, age, and the like. Therefore, the above dosage does not limit the scope of the present invention in any aspect.

The composition can be administered to mammals such as rat, mice, livestock, humans, and the like by various routes. All modes of administration can be expected, for example by oral, rectal or intravenous, intramuscular, subcutaneous, intrauterine dural or intracerebroventricular injection.

Hereinafter, the present invention will be described in detail with reference to the following examples. The examples are only for describing the present invention in more detail and it is obvious to those skilled in the art that that the scope of the present invention is not limited by these examples embodiments in accordance with the gist of the present invention.

Example 1 Construction of Humanized Anti-DR4 scFv Antibody Gene Specific to Human Death Receptor (DR4)

DR4 is a kind of death receptor that induces apoptosis in cells and is an antigen expressed in various cancer cells. Death receptors, such as DR4, are receptors that induce apoptosis in which cells die by binding to TNF-related apoptosis inducing ligand (TRAIL) at the cell surface.

In order to clone the antigen-binding site (scFv) gene of the antibody that specifically binds to human DR4, scFv antibody protein that specifically binds to human DR4 protein was isolated from various scFv antibody libraries in chickens. In the amino acid sequence of the chicken scFv antibody protein, the amino acids of the complementarity-determining region (CDR) and the amino acids of the Vernier zone were preserved, and the remaining amino acid sequence was replaced with the amino acids of the human scFv antibody to determine the humanized DR4 scFv antibody amino acid sequence. The humanized DR4 scFv antibody amino acid sequence (SEQ ID NO: 1) was shown in FIG. 1(A).

Next, the humanized DR4 scFv antibody amino acid sequence was applied for a codon sequence optimized for human cells to determine a sequence capable of producing a scFv recombinant protein specific DR4 in human cells. The nucleotide sequence (SEQ ID NO: 2) was shown in FIG. 1(B).

Example 2: Gene Structure Synthesis of Secretory (Soluble Form) Humanized DR4 scFv Antibody Fragment Recombinant Protein Referring to FIG. 2, a nucleotide sequence of an isoleucine zipper (ILZ) peptide was added to the 3' end of the humanized DR4 scFv antibody gene to enable the synthesis of a trimolecular complex of scFv protein. DR4 protein expressed on the cell surface is present in the form of a complex of three molecules (DR4 trimer) not one molecule, and as a result, the trimolecular complex is known to transmit apoptosis signal by reacting with the TRAIL complex. In addition, to the 5 terminal of the DR4 scFv antibody gene, a leader sequence of the CD8α chain and other sequences corresponding to the Flag tag, IgG3 hinge and His6 tag were added to secrete the scFv protein from cells. Flag tag and His6 tag were added for purification and identification of secretory DR4 scFv antibody protein, and IgG3 Hinge was added to give structural flexibility for DR4 scFv antibody protein to bind well into trimolecular complex.

The antibody gene structure for the formation of a trimolecular complex of a secretory recombinant protein containing a humanized DR4 scFv antibody fragment was shown in FIG. 2(A), and its complete nucleotide sequence (SEQ ID NO: 3) and the nucleotide sequence of each domain were shown in FIG. 2(B). Domains include the leading sequence of the CD8α chain (SEQ ID NO: 4), humanized DR4 scFv antibody sequence (SEQ ID NO: 2), Flag tag sequence (SEQ ID NO: 5), IgG3 hinge sequence (SEQ ID NO: 6), isoleucine zipper (ILZ) peptide sequence (SEQ ID NO: 7) and His6 tag sequence (SEQ ID NO: 8).

Example 3: Confirmation of Secretion of Secretory Humanized DR4 scFv Antibody Fragment Recombinant Protein Referring to FIG. 3(A), after synthesizing a gene of a secretory humanized DR4 scFv antibody recombinant protein using a gene synthesis method, pCMVFL-srkDR4 clones were obtained by cloning the synthesized artificial gene into a p3XFLAG-CMV14 vector, which is an eukaryotic expression vector. The pCMVFL-srkDR4 DNA was transfected into HEK293 cells using Lipofector-EXT Reagent (APTABIO, Korea), and cultured in a medium without serum to collect the culture solution.

The collected culture solution was purified by HisPur Cobalt Resin (Thermo Scientific, USA), and the presence of humanized DR4 scFv antibody recombinant protein was confirmed by Western blotting using an antibody against a Flag tag. As a result, referring to FIG. 3(B), No. 1 is a DR4 scFv antibody recombinant protein purified using His tag, and No. 2 is a DR4 scFv antibody recombinant protein secreted in the culture medium of the transformed cell. It was confirmed that the DR4 scFv antibody recombinant protein secreted into the culture medium outside the cell had a size of about 30 kDa, which corresponded to the molecular weight of the protein estimated from the humanized DR4 scFv antibody gene.

Example 4: Apoptosis Inducing Effect of Secretory Humanized DR4 scFv Antibody Fragment Recombinant Protein Although the DR4 antibody binds to the DR4 protein, the DR4 antibody may only bind to the DR4 protein and fail to induce apoptosis signals from DR4. Therefore, in order to prepare a dual-acting CAR-T cell therapeutic agent having cytotoxicity by CTL while inducing apoptosis signaling from DR4, it has to be confirmed that the secretory humanized DR4 scFv antibody recombinant protein prepared in the present invention has the effect of inducing apoptosis of cancer cells expressing DR4.

To this end, apoptosis-inducing effects of secretory humanized DR4 scFv antibody recombinant protein were analyzed using HeLa cells, a cervical cancer cell line expressing DR4 on the cell surface, and HCT-116 cells, a colon cancer cell line. HEK293 cells which do not express DR4 on the cell surface were used as a control. Each of these three cells was inoculated in a culture dish and cultured overnight, and then the secretory humanized DR4 scFv antibody recombinant protein was added to the culture medium, and the degree of death of the cells during culturing was determined by MTT method (Cyto X™ Cell viability assay kit, LPS solution, Korea).

As a result, referring to FIG. 4(A), apoptosis effect by the secretory humanized DR4 scFv antibody recombinant protein was not observed in HEK293 cells which do not express DR4, while referring to FIG. 4(B) and FIG. 4(C), it was confirmed that apoptosis increased in proportion to the concentration of humanized DR4 scFv antibody recombinant protein in HeLa cells and HCT-116 cells, which express DR4. These results indicate that DR4 scFv antibody recombinant protein obtained from pCMVFL-srkDR4 DNA is secreted as a trimolecular complex capable of binding to the DR4 trimer and the DR4 scFv antibody recombinant protein binds to DR4 on the surface of cancer cells and transmits apoptosis signals into the inside of the cancer cells.

Example 5: Preparation of Chimeric Antigen Receptor Expression Vectors Comprising Humanized DR4 scFv Antibody Fragments In the above example, it was confirmed that the secretory humanized DR4 scFv antibody recombinant protein forms a trimolecular complex, which binds to the DR4 trimer on the surface of the cancer cell and transmits a death signal to the cancer cell. These results suggest that if the genetic construct of the secretory humanized DR4 scFv antibody recombinant protein of the present invention can be modified and expressed on the surface of CTL, it may be utilized as a dual-acting chimeric antigen receptor (CAR)-T) cell therapeutic agent which simultaneously shows the apoptosis signal of the cancer cells and the cytotoxic action of CTL through DR4.

Therefore, referring to FIG. 5(A), a transmembrane region (CD8α TM) was added to 3-terminal of the secretory humanized DR4 scFv antibody recombinant protein gene so that the DR4 protein can bind to the cell membrane. In addition, DR4 specific CAR gene construct in which the cytotoxic activation signaling region (4-1BB/CD3 zeta) of CTL is linked was synthesized so as to exhibit cytotoxic action to cancer cells by CAR-T cells.

The complete nucleotide sequence of the humanized DR4 scFv antibody CAR of about 1,600 bp size synthesized from the nucleotide sequence of the DR4 specific CAR gene construct and the nucleotide sequence of each domain were shown in FIG. 5(B) and FIG. 6. The domain consists of leading sequence of the CD8α chain (SEQ ID NO: 4), humanized DR4 scFv antibody sequence (SEQ ID NO: 2), IgG3 hinge sequence (SEQ ID NO: 6), isoleucine zipper (ILZ) peptide sequence (SEQ ID NO: 7), CD8α hinge sequence (SEQ ID NO: 10), CD8α TM sequence (SEQ ID NO: 11), 4-1BB signal sequence (SEQ ID NO: 12), and CD3 zeta signal sequence (SEQ ID NO: 13).

Example 6: Cytotoxic Effect of Chimeric Antigen Receptor Expressing Lymphocytes Comprising Humanized DR4 scFv Antibody Fragment In order to confirm whether CTL cells expressing the DR4 specific chimeric antigen receptor on the cell surface induce apoptosis of the cancer cells, cells expressing the DR4 specific CAR gene construct of FIG. 5(A) on the lymphocyte surface were prepared.

To this end, a pCMVFL-rkDR4CAR clone was prepared by inserting a CAR gene into a plasmid vector capable of expressing in eukaryotic cells as shown in FIG. 7 and inserting the DR4 specific CAR gene of FIG. 5(A) into the p3XFLAG-CMV14 vector, which is an eukaryotic expression vector. After transforming the pCMVFL-rkDR4CAR clone DNA into splenocytes of mice, lymphocytes expressing DR4 specific CARs were prepared, and analyzed whether these cells induce apoptosis of the cancer cells expressing DR4 on the cell surface.

Lymphocytes were isolated from spleens of mice, and then PCMVFL-rkDR4CAR clone DNA was injected into lymphocytes using the jetPEI® DNA Transfection Reagent of Polyplus Transfection (New York, N.Y., USA), referring to the protocol provided by the manufacturer. After incubating the cells in which clone DNA was injected for 24 hours at 37° C., the cells were collected and suspended in DMEM medium containing 10% fetal bovine serum (FBS) to be a concentration of $10^6$ cells/ml to obtain lymphocytes expressing DR4 specific CAR and effector cell suspensions showing cytotoxicity were prepared.

These cells were mixed and cultured with HeLa cells, which are DR4 expressing cancer cells, or HEK293 cells, which are human embryonic cell lines not expressing DR4 and cytotoxic effects were compared. The degree of killing of target cells was analyzed using CellTox Green Cytotoxicity Assay kit of Promega (Madison, Wis., USA) referring to a protocol provided by the manufacturer. This kit is a suitable assay for measuring the cytotoxicity of lymphocytes expressing DR4 specific CARs by measuring cytotoxicity by the fluorescence properties exhibited from that when DNA is exposed by the killing of target cells, CellTox Green fluorescent dye binds to the exposed DNA. To this end, HeLa cells and HEK293 cells used as target cells are suspended in DMEM medium containing 10% fetal calf serum to a concentration of $10^5$ cells/ml, respectively and then mixed with 2 μl/ml of Cell Tox Green Dye and each well was inoculated with 100 μl ($10^4$ cells/well). After about 24 hours of incubation, the target cells were attached to the culture dish, and then 100 μl of effector cell suspension ($10^5$ effector cells) was added to each well to analyze cytotoxicity against the target cells (UT ratio=10:1). At this time, culture medium with only the target cells and without the effector cells was used as a control. After culturing for 3 days, the amount of fluorescence in the culture solution was measured using a Fluorescence Multi-Detection Reader of BioTek (Winooski, Vt., USA), and then the amount of fluorescence generated by cytotoxicity was compared by correcting the amount of fluorescence in the control group.

As a result, referring to FIG. 8, the amount of fluorescence was low after DR4 specific CAR expressing lymphocytes and HEK293 cells that did not express DR4 (line 1) were mixed and cultured, while the fluorescence was relatively high 2-3 times after HeLa cells expressing DR4 specific CAR expressing lymphocytes and DR4 (line 2) were mixed and cultured. These results indicate that lymphocytes expressing DR4 specific CARs transformed with the pCMVFL-rkDR4CAR plasmid vector of FIG. 7 selectively induce cytotoxicity in cells expressing DR4. This suggests that the DR4-specific CAR gene construct of FIG. 5(A) can express a DR4-specific CAR receptor protein on the cell surface of lymphocytes and this receptor can bind to DR4 protein on the surface of cancer cells to exhibit the cytotoxicity.

Recombinant viruses need to be used to facilitate the injection of the DR4 specific CAR gene construct of FIG. 5(A) into T cells. In the present invention, a recombinant virus vector pAAV-rkDR4CAR clone in which a DR4 specific CAR gene construct was coupled to an adeno-associated virus (AAV) expression vector as shown in FIG. 9 was constructed. When the AAV virus particles are produced using the pAAV-rkDR4CAR clone and infected with CTL cells, the infected T cells are converted to CAR-T cells expressing DR4 scFv antibody of a trimolecular complex on the cell surface, and as shown in FIG. 10, dual-acting CAR-T cells which simultaneously show the induction of apoptosis of cancer cells through DR4 and the cytotoxic effect of CTL can be obtained with high efficiency.

While the present invention has been particularly described with reference to specific embodiments thereof, it is apparent that this specific description is only a preferred embodiment and that the scope of the present invention is not limited thereby to those skilled in the art. That is, the practical scope of the present invention is defined by the appended claims and their equivalents.

The scope of the present invention is represented by the following claims, and it should be construed that all changes or modifications derived from the meaning and scope of the claims and their equivalents of the claims are included in the scope of the present invention.

The invention claimed is:

1. A gene expression cassette encoding an anti-DR4 antibody fragment recombinant protein, wherein the anti-DR4 antibody fragment recombinant protein comprises an anti-DR4 antibody fragment domain having the amino acid sequence of SEQ ID NO: 1 which specifically binds to a death receptor (DR4), a trimolecular complex forming domain, a secretory inducing domain, a transmembrane domain and a signaling domain.

2. The gene expression cassette of claim 1, wherein the anti-DR4 antibody fragment recombinant protein is a chimeric antigen receptor (CAR).

3. The gene expression cassette of claim 1, wherein the anti-DR4 antibody fragment is selected from the group consisting of scFv, (scFv)2, Fab, Fab' and F(ab')2.

4. The gene expression cassette of claim 1, wherein the gene expression cassette has the nucleotide sequence of SEQ ID NO: 9.

5. A vector comprising the gene expression cassette of claim 1.

6. The vector of claim 5, wherein the vector is a recombinant plasmid vector or a recombinant viral vector.

7. The vector of claim 6, wherein the recombinant viral vector is selected from the group consisting of adenovirus vectors, adeno-associated viral vectors, lentivirus vectors and retroviral vectors.

8. A chimeric antigen receptor expressing cell transformed with the vector of claim 5.

9. The chimeric antigen receptor expressing cell of claim 8, wherein the chimeric antigen receptor expressing cell is a chimeric antigen receptor expressing T (CAR-T) cell or a natural killer (CAR-NK) cell.

10. The gene expression cassette of claim 1, wherein the anti-DR4 antibody fragment domain has the nucleotide sequence of SEQ ID NO: 2.

* * * * *

SEQUENCE LISTING

```
<160> NUMBER OF SEQ ID NOS: 13

<210> SEQ ID NO 1
<211> LENGTH: 249
<212> TYPE: PRT
<213> ORGANISM: Artificial Sequence
<220> FEATURE:
<223> OTHER INFORMATION: humanized DR4 scFv Ab

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Thr Phe Ser Ser Tyr
            20                  25                  30

Ser Met Gln Trp Val Arg Gln Ala Pro Gly Lys Gly Leu Glu Tyr Val
        35                  40                  45

Ala Gly Ile Arg Ser Asp Gly Arg Tyr Thr Asn Tyr Gly Ala Ala Val
    50                  55                  60

Lys Gly Arg Ala Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Lys Gly Ala Tyr Gly Tyr Cys Gly Ser Thr Cys Ala Pro Tyr Leu
            100                 105                 110

Gly Gln Ile Asp Ala Trp Gly Gln Gly Thr Leu Val Thr Val Ser Ser
        115                 120                 125

Gly Ser Thr Ser Gly Ser Gly Lys Pro Gly Ser Gly Glu Gly Ser Thr
    130                 135                 140

Lys Gly Ser Tyr Glu Leu Thr Gln Pro Pro Ser Val Ser Val Ser Pro
145                 150                 155                 160

Gly Gln Thr Val Arg Ile Thr Cys Ser Gly Gly Arg Tyr Thr Tyr Gly
                165                 170                 175

Trp Phe Gln Gln Lys Pro Gly Gln Ala Pro Val Thr Val Ile Tyr Gly
            180                 185                 190

Asn Asp Lys Arg Pro Ser Asn Ile Pro Ser Arg Phe Ser Gly Ser Thr
        195                 200                 205

Ser Gly Ser Thr Val Thr Leu Thr Ile Ser Gly Val Gln Ala Glu Asp
    210                 215                 220

Glu Ala Asp Tyr Tyr Cys Gly Gly Ala Asp Phe Ser Ala Gly Leu Phe
225                 230                 235                 240
```

-continued

Gly Gly Gly Thr Lys Leu Thr Val Leu
245

<210> SEQ ID NO 2
<211> LENGTH: 747
<212> TYPE: DNA
<213> ORGANISM: Artificial Sequence
<220> FEATURE:
<223> OTHER INFORMATION: humanized DR4 scFv Ab

<400> SEQUENCE: 2
gaagtccaac ttgtagaatc aggcggcggg ctcgtacagc ccggtggaag ccttagactt 60
tcttgttcag cctcagggtt tacattctcc agttactcca tgcaatgggt gcggcaagcg 120
cccggaaaag ggcttgaata cgtggcgggt atcagaagcg acggtcgata tacaaactac 180
ggcgctgcgg taaaaggccg cgctaccata tctcgcgata actcaaagaa taccgtctat 240
ctccagatga acagccttag agcggaagat accgcagtgt attattgtgc taagggtgca 300
tacggttact gtggatctac ctgtgcaccg tacctcggcc agatagatgc atgggggcaa 360
ggcacgttgg tcactgtatc aagtgggagc acttctggaa gtgggaagcc tgggagcggg 420
gaaggcagca ccaaaggttc atatgagctt acccaacctc cgtccgtctc cgttagccca 480
ggtcagacag ttagaataac ctgcagtgga ggacgataca cgtacggctg gtttcaacaa 540
aagccggggc aagcgccggt gacagttatc tatgggaatg ataaaaggcc atctaatata 600
ccgtctcgat tttcaggctc tacttctggc agtactgtaa cactcacgat tagtggggtc 660
caagcagaag atgaggcaga ctattactgc gggggcgcag atttctcagc gggccttttt 720
ggagggggta caaagctcac ggtgctg 747

<210> SEQ ID NO 3
<211> LENGTH: 999
<212> TYPE: DNA
<213> ORGANISM: Artificial Sequence
<220> FEATURE:
<223> OTHER INFORMATION: humanized DR4 scFv Ab recombinant protein

<400> SEQUENCE: 3
atggccttgc ctgttactgc gttgctgctg ccccttgcac tgttgctcca cgcggccaga 60
ccagaagtcc aacttgtaga atcaggcggc gggctcgtac agcccggtgg aagccttaga 120
ctttcttgtt cagcctcagg gtttacattc tccagttact ccatgcaatg ggtgcggcaa 180
gcgcccggaa aagggcttga atacgtggcg ggtatcagaa gcgacggtcg atatacaaac 240
tacggcgctg cggtaaaagg ccgcgctacc atatctcgcg ataactcaaa gaataccgtc 300
tatctccaga tgaacagcct tagagcggaa gataccgcag tgtattattg tgctaagggt 360
gcatacggtt actgtggatc tacctgtgca ccgtacctcg gccagataga tgcatggggg 420
caaggcacgt tggtcactgt atcaagtggg agcacttctg gaagtgggaa gcctgggagc 480
ggggaaggca gcaccaaagg ttcatatgag cttacccaac ctccgtccgt ctccgttagc 540
ccaggtcaga cagttagaat aacctgcagt ggaggacgat acacgtacgg ctggtttcaa 600
caaaagccgg ggcaagcgcc ggtgacagtt atctatggga atgataaaag gccatctaat 660
ataccgtctc gattttcagg ctctacttct ggcagtactg taacactcac gattagtggg 720
gtccaagcag aagatgaggc agactattac tgcgggggcg cagatttctc agcgggcctt 780
tttggagggg gtacaaagct cacggtgctg gccgcagccg actacaagga tgacgatgat 840
aagggggcgg caccgaaacc atccacaccg cccggcagct cacggatgaa gcaaattgaa 900

-continued gacaagattg aagaaatact tagtaagatt taccatatcg aaaacaaaat cgctcgcatt 960
aagaaactta taggtgaacg ccatcaccac caccaccac 999

<210> SEQ ID NO 4
<211> LENGTH: 63
<212> TYPE: DNA
<213> ORGANISM: Artificial Sequence
<220> FEATURE:
<223> OTHER INFORMATION: CD8 alpha leader sequence

<400> SEQUENCE: 4
atggccttgc ctgttactgc gttgctgctg ccccttgcac tgttgctcca cgcggccaga 60
cca 63

<210> SEQ ID NO 5
<211> LENGTH: 36
<212> TYPE: DNA
<213> ORGANISM: Artificial Sequence
<220> FEATURE:
<223> OTHER INFORMATION: FLAG sequence

<400> SEQUENCE: 5
gccgcagccg actacaagga tgacgatgat aagggg 36

<210> SEQ ID NO 6
<211> LENGTH: 39
<212> TYPE: DNA
<213> ORGANISM: Artificial Sequence
<220> FEATURE:
<223> OTHER INFORMATION: IgG3 hinge sequence

<400> SEQUENCE: 6
gcggcaccga aaccatccac accgcccggc agctcacgg 39

<210> SEQ ID NO 7
<211> LENGTH: 96
<212> TYPE: DNA
<213> ORGANISM: Artificial Sequence
<220> FEATURE:
<223> OTHER INFORMATION: ILZ sequence

<400> SEQUENCE: 7
atgaagcaaa ttgaagacaa gattgaagaa atacttagta agatttacca tatcgaaaac 60
aaaatcgctc gcattaagaa acttataggt gaacgc 96

<210> SEQ ID NO 8
<211> LENGTH: 18
<212> TYPE: DNA
<213> ORGANISM: Artificial Sequence
<220> FEATURE:
<223> OTHER INFORMATION: His6 sequence

<400> SEQUENCE: 8
catcaccacc accaccac 18

<210> SEQ ID NO 9
<211> LENGTH: 1614
<212> TYPE: DNA
<213> ORGANISM: Artificial Sequence
<220> FEATURE:
<223> OTHER INFORMATION: humanized DR4 scFv Ab CAR

<400> SEQUENCE: 9

-continued

```
atggccttgc ctgttactgc gttgctgctg ccccttgcac tgttgctcca cgcggccaga      60
ccagaagtcc aacttgtaga atcaggcggc gggctcgtac agcccggtgg aagccttaga     120
ctttcttgtt cagcctcagg gtttacattc tccagttact ccatgcaatg ggtgcggcaa     180
gcgcccggaa aagggcttga atacgtggcg ggtatcagaa gcgacggtcg atatacaaac     240
tacggcgctg cggtaaaagg ccgcgctacc atatctcgcg ataactcaaa gaataccgtc     300
tatctccaga tgaacagcct tagagcggaa gataccgcag tgtattattg tgctaagggt     360
gcatacggtt actgtggatc tacctgtgca ccgtacctcg gccagataga tgcatggggg     420
caaggcacgt tggtcactgt atcaagtggg agcacttctg gaagtgggaa gcctgggagc     480
ggggaaggca gcaccaaagg ttcatatgag cttacccaac ctccgtccgt ctccgttagc     540
ccaggtcaga cagttagaat aacctgcagt ggaggacgat acacgtacgg ctggtttcaa     600
caaaagccgg ggcaagcgcc ggtgacagtt atctatggga atgataaaag gccatctaat     660
ataccgtctc gattttcagg ctctacttct ggcagtactg taacactcac gattagtggg     720
gtccaagcag aagatgaggc agactattac tgcgggggcg cagatttctc agcgggcctt     780
tttggagggg gtacaaagct cacggtgctg gcggcaccga aaccatccac accgcccggc     840
agctcacgga tgaagcaaat tgaagacaag attgaagaaa tacttagtaa gatttaccat     900
atcgaaaaca aaatcgctcg cattaagaaa cttataggtg aacgcaccac gaccccagca     960
ccacggccgc cgactccggc cccgacgata gcctcacaac ctctgtcttt gcgccctgaa    1020
gcgtgccgac ctgcagcagg cggtgccgta catacgagag ggctggattt tgcttgcgac    1080
atttatattt gggctcccct cgcagggaca tgtggcgtat tgcttctctc tctcgtgatc    1140
acgctctatt gcaaaagggg gcgaaagaag ttgctgtata tctttaaaca accatttatg    1200
agaccagtgc aaacaacgca ggaggaagat ggctgtagct gtaggttccc cgaagaggag    1260
gaaggaggct gcgaactcag ggttaagttc agtagatctg cggatgctcc cgcgtatcag    1320
cagggccaga atcagcttta caatgaactc aatcttggcc gccgagaaga gtatgatgtg    1380
ctcgacaagc gccgcggcag agaccccgaa atgggaggta agcccaggag aaaaaatccg    1440
caggaaggtc tttacaacga attgcaaaag gacaagatgg cagaagcata ctcagagatt    1500
ggtatgaaag gtgaacggcg acgcgggaaa ggacatgacg gcctttatca aggactctca    1560
accgctacta aagatactta cgacgcgctc cacatgcagg ctctgccacc gcgc          1614
```

<210> SEQ ID NO 10
<211> LENGTH: 135
<212> TYPE: DNA
<213> ORGANISM: Artificial Sequence
<220> FEATURE:
<223> OTHER INFORMATION: CD8 alpha hinge sequence

<400> SEQUENCE: 10

```
accacgaccc cagcaccacg gccgccgact ccggccccga cgatagcctc acaacctctg      60
tctttgcgcc ctgaagcgtg ccgacctgca gcaggcggtg ccgtacatac gagagggctg     120
gattttgctt gcgac                                                      135
```

<210> SEQ ID NO 11
<211> LENGTH: 72
<212> TYPE: DNA
<213> ORGANISM: Artificial Sequence
<220> FEATURE:
<223> OTHER INFORMATION: CD8 alpha TM sequence

<400> SEQUENCE: 11

-continued

```
atttatattt gggctcccct cgcagggaca tgtggcgtat tgcttctctc tctcgtgatc     60

acgctctatt gc                                                         72


<210> SEQ ID NO 12
<211> LENGTH: 126
<212> TYPE: DNA
<213> ORGANISM: Artificial Sequence
<220> FEATURE:
<223> OTHER INFORMATION: 4-1BB signal sequence

<400> SEQUENCE: 12

aaaagggggc gaaagaagtt gctgtatatc tttaaacaac catttatgag accagtgcaa     60

acaacgcagg aggaagatgg ctgtagctgt aggttccccg aagaggagga aggaggctgc    120

gaactc                                                               126


<210> SEQ ID NO 13
<211> LENGTH: 336
<212> TYPE: DNA
<213> ORGANISM: Artificial Sequence
<220> FEATURE:
<223> OTHER INFORMATION: CD3 zeta Signal sequence

<400> SEQUENCE: 13

agggttaagt tcagtagatc tgcggatgct cccgcgtatc agcagggcca gaatcagctt     60

tacaatgaac tcaatcttgg ccgccgagaa gagtatgatg tgctcgacaa gcgccgcggc    120

agagaccccg aaatgggagg taagcccagg agaaaaaatc cgcaggaagg tctttacaac    180

gaattgcaaa aggacaagat ggcagaagca tactcagaga ttggtatgaa aggtgaacgg    240

cgacgcggga aaggacatga cggcctttat caaggactct caaccgctac taaagatact    300

tacgacgcgc tccacatgca ggctctgcca ccgcgc                              336
```